(12) United States Patent
Dascalu

(10) Patent No.: US 8,680,134 B2
(45) Date of Patent: Mar. 25, 2014

(54) TRIPTANS FOR THE TREATMENT OF PSORIASIS

(76) Inventor: Avi Dascalu, Tel-Aviv (IL)

(*) Notice: Subject to any disclaimer, the term of this patent is extended or adjusted under 35 U.S.C. 154(b) by 0 days.

(21) Appl. No.: 13/503,418

(22) PCT Filed: Oct. 22, 2010

(86) PCT No.: PCT/IB2010/002881
§ 371 (c)(1),
(2), (4) Date: Jun. 21, 2012

(87) PCT Pub. No.: WO2011/048496
PCT Pub. Date: Apr. 28, 2011

(65) Prior Publication Data
US 2012/0252863 A1    Oct. 4, 2012

Related U.S. Application Data

(60) Provisional application No. 61/254,258, filed on Oct. 23, 2009.

(51) Int. Cl.
*A01N 43/38* (2006.01)
*A61K 31/405* (2006.01)
*C07D 209/14* (2006.01)
*C07D 209/16* (2006.01)

(52) U.S. Cl.
USPC ......................................... 514/415; 548/506

(58) Field of Classification Search
None
See application file for complete search history.

(56) References Cited

U.S. PATENT DOCUMENTS

| 5,320,777 | A  | * | 6/1994  | Nguyen et al. | 516/133 |
| 6,361,806 | B1 | * | 3/2002  | Allen | 424/740 |
| 7,135,164 | B2 | * | 11/2006 | Rojanapanthu et al. | 424/58 |
| 2004/0214861 | A1 | * | 10/2004 | Seibert | 514/314 |
| 2007/0207222 | A1 |   | 9/2007  | Yu et al. | |

FOREIGN PATENT DOCUMENTS

| EP | 0904777 | 3/1999 |
| WO | WO0006161 | 2/2000 |
| WO | WO03032983 | 4/2003 |
| WO | WO2004093826 | 4/2004 |
| WO | WO2004112723 | 12/2004 |
| WO | WO2006074114 | 7/2006 |
| WO | WO2007047486 | 4/2007 |

OTHER PUBLICATIONS

Aggarwal et al. Antimicrobial activity profiles of the two enantiomers of limonen and carvone isolated from the oils of Mentha spicata and Anethum sowa. Flavour Fragr. J. 2002, 17: 59-63.*
Edmeads, J.G. et al. "Tolerability profile of zolmitriptan (Zomig; 311C90), a novel dual central and peripherally acting 5HT1B/1D agonist." Cephalagia, 1997 Suppl 18: 41-52.
Femenia-Font, A. et al. "Effect of chemical enhancers on the in vitro percutaneous absorption of sumatriptan succinate." European Journal of Pharmaceutics and Biopharmaceutics, vol. 61, No. 1-2, Sep. 1, 2005, pp. 50-55.
Femenia-Font, A. et al. "Combination strategies for enhancing transdermal absorption of sumatriptan through skin." International Journal of Pharmaceutics, vol. 323: 125-30 No. 1-2, Oct. 12, 2006.
Gudjonsson, J.E. et al. "Immunopathogenic mechanisms in psoriasis." Clin Exp Immunol. 2004 135 (1):1-8.
Lin, L.T.P. et al. "Onset of psoriasis during therapy with fluoxetine." General Hospital Psychiatry, (2010) 32: 446e9-446.e10.
McFadden, J. et al. "Cross reactivity between streptococcal M surface antigen and human skin." Br J Dermatol, 1991, 125 (5):443-7.
Nestle, F.O. et al. Psoriasis New Eng J Med vol. 2009, 361 (5); 496-509.
Nordlind, K. et al. "Expression of serotonergic receptors in psoriatic skin." Arch Dermatol Res, (2006) 298; 99-106.
Pierce, M. et al. "A Novel Transdermal Formulation of Sumatriptan." Headache, 2009, 49 (6):817-825.
Schon, M.P. et al. Psoriasis. New Eng J Med. 2005, 352 (18):1899-1912.
SDS No. 128214 Sumatriptan, Safety Data Sheet, GlaxoSmithKlein 2004.
SDS No. 110533 Narariptan, Safety Data Sheet, GlaxoSmithKlein 2008.
Slominski, A. et al. "Functional Activity of Serotoninergic and Melatoninergic Systems Expressed in the Skin." Journal of Cellular Physiology, (2003) 196: 144-153.
Thorslund, K. et al. "The serotonin transporter protein is expressed in psoriasis, where it may play a role in regulating apoptosis." Arch Dermatol Res, (2009) 301: 449-457.

* cited by examiner

*Primary Examiner* — Anna Pagonakis
(74) *Attorney, Agent, or Firm* — Marianne Fuierer; Moore & Van Allen, PLLC

(57) ABSTRACT

The present invention provides for a composition comprising a tryptamine based drug that acts as a 5-hydroxytryptamine-1 inhibitor in an amount sufficient to reduce the effects of psoriasis and wherein the composition is formulated for topical or oral administration.

3 Claims, 1 Drawing Sheet

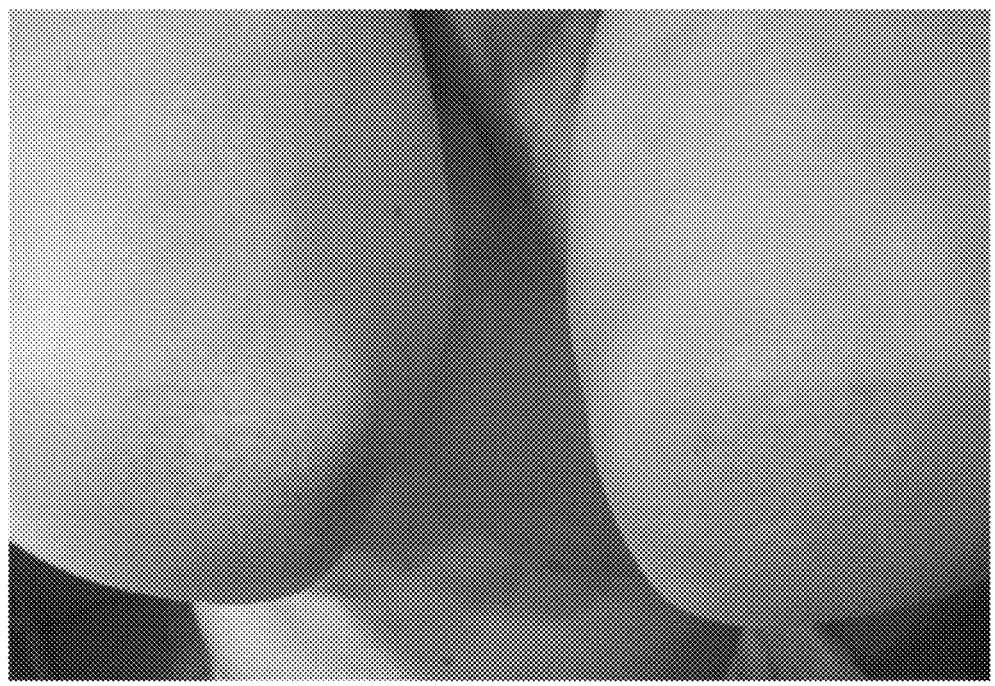

TRIPTANS FOR THE TREATMENT OF PSORIASIS

CROSS-REFERENCE TO RELATED APPLICATION

The present PCT International application and invention claims priority to U.S. Provisional Application No. 61/254,258 filed on Oct. 23, 2009, the contents of which are incorporated by reference herein for all purposes.

BACKGROUND OF THE INVENTION

1. Field of the Invention

The present invention relates to compositions and method of treatment for psoriasis and more particularly to the topical use of a tryptamine based drug that acts as a 5-hydroxytryptamine-1 inhibitor.

2. Related Art in the Field

Psoriasis is a widespread squamous skin disease and a chronic ailment affecting about 2-3% of worldwide population at a various extent. It presents as silvery scales on an erythematic base, especially on extensor surfaces, but it can affect as well the scalp, face, nails and flexors or intretigineous areas. Its presentation varies from confluent areas to pustular, guttate or annular. Skin symptoms may be either local or systemic, affecting the body as an acute, recurrent or chronic disease.

The pathophysiology of Psoriasis Vulgaris is immunologic and genetic (Gudjonsson J E et al; Schön and Boehncke). Skin lesions are considered to evolve due to a genetic tendency of the skin to react to internal hormonal stress and/or external environmental stress which cause an exacerbation (Nestle et al). A particular attention should be given to onset of psoriasis or its exacerbation due to post streptococcal infection which is generated by antigenic cross-reactivity between a surface antigen and human skin (McFadden et al). The pathological process of psoriasis involves a T lymphocyte infiltrate reaction in the epidermis and parakeratosis, and the disease is characterized as a T cell reactivity disease with disregulation.

Current treatment of Psoriasis Vulgaris is partially effective. Treatment involves chronic administration of drugs that might cause numerous undesirable side-effects due to safety issues of prolonged term administration of present treatments. For example, topical treatments using specific compounds might induce side effects, such as: steroids producing steroidal side effects; Vitamin D3 analogues—calcipotriol, low efficacy compound with irritant effect; Vitamin A derivatives, e.g. tazarotene, which are irritants and teratogenic; Immunologic agents—e.g. tacrolimus, pimecrolimus which might cause immunological suppression; local sensitisers such as Dithranol which can only be used for a short time due to irritation; and coal tar which is efficacious but with long term risk of tumors.

Systemic treatments which are currently in common dermatological use include: Phototherapy, such as UVB and PUVA which may induce potentially carcinogenic radiation; Cyclosporine A, known to cause severe immunologic side effects and tumors; Methotrexate which is an immunologic suppressant; Acitretin which is not only teratogenic but also an irritant potent cholesterol eleavanting agent; Fumaric acid which causes a high incidence of gastro intestinal side effects; Purine manipulation using Mycophenolate, 6-thioguanine whch has not been shown to be effective and biological treatments which includes the administration of Alefacept, Efalizumab, or Infliximab which are not considered to be safe on the long range.

A mild subject suffering from Psoriasis Vulgaris is usually treated at the start by a steroid alone or in combination with calcipotriol. A subject suffering from a moderate condition may need the addition of one of the systemic agents or combined phototherapy, depending of the areas of involvement. Severe causes are generally treated by oral acitretin or phototherapy and by hospitalization.

A definitive, highly efficacious, fast acting and low side effects solution is lacking for the treatment of psoriasis. Hence, it is desired in the art to provide an effective treatment that overcomes the problems associated with current methods of treatment.

SUMMARY OF THE INVENTION

The present invention provides compositions and topical methods of treating a subject suffering from a skin disorder selected from the group consisting of psoriasis, acne, atopic dermatitis, eczema, rosacea, actinic keratosis, seborrheic dermatitis, and congenital keratinization disorders, wherein the composition comprises at least one a tryptamine based drug that acts as a 5-hydroxytryptamine-1 inhibitor in a therapeutically effective amount to treat such skin disorder.

Preferably the skin condition is psoriasis because there is a particular need to provide compositions and methods of treatment that: (i) rapidly improve the clinical condition; (ii) can be used topically, improving convenience and safety; (iii) are devoid of retinoid and steroid undesirable side effects; (iv) can be used by women at childbirth ages without long term teratogenic effects and even during lactation periods; and (v) can be used as a local scalp treatment.

The present invention provides for the topical use of triptans that is surprisingly effective and provides the advantages set forth above. Triptans are tryptamine based drugs acting as selective 5 Hydroxytryptamine-1 inhibitors and heretofore have been extensively used for the treatment of migraine or headache. Examples of drugs of this class include but are not limited to:

Sumatriptan, 1-[3-(2-Dimethylaminoethyl)-1H-indol-5-yl]-N-methyl-methanesulfonamide, CAS registry number 103628-46-2, or combined with succinate 1-[3-(2-Dimethylaminoethyl)-1H-indol-5-yl]-N-methyl-methanesulfonamide succinate CAS registry number 103628-48-4;

rizatriptan N,N-Dimethyl-5-(1H-1,2,4-triazol-1-ylmethyl)-1H-indole-3-ethanamine; N,N-Dimethyl-2-[5-(1,2,4-triazol-1-ylmethyl)-1H-indol-3-yl]ethanamine CAS registry number 144034-80-0;

rizatriptan combined with benzoate, N,N-Dimethyl-2-[5-(1,2,4-triazol-1-ylmethyl)-1H-indol-3-yl]ethylamine benzoate CAS registry number 145202-66-0;

naratriptan N-methyl-2-[3-(1-methylpiperidin-4-yl)-1H-indol-5-yl]ethanesulfonamide Hydrochloride CAS registry number 143388-64-1;

zolmitriptan (4S)-4-[[3-(2-dimethylaminoethyl)-1H-indol-5-yl]methyl]-1,3-oxazolidin-2-one, CAS registry number 139264-17-8;

eletriptan 3-[(1-Methylpyrrolidin-2-yl)methyl]-5-(2-phenylsulfonylethyl)-1H-indole CAS registry number 143322-58-1;

eletriptan hydrobromise3-(((2R)-1-Methyl-2-pyrrolidinyl))methyl)-5-(2-(phenylsulfonyl)ethyl)-1H-indole hydrobromide CAS registry number 177834-92-3;

almotriptan N,N-Dimethyl-2-[5-(pyrrolidin-1-ylsulfonyl-methyl)-1H-indol-3-yl]ethanamine CAS registry number 181183-52-8;

N,N-Dimethyl-2-[5-(pyrrolidin-1-ylsulfonylmethyl)-1H-indol-3-yl]-ethanamine CAS 154323-57-6; and frovatriptan CAS registry number 158747-02-5.

Generally, effective triptans may be selected from a group consisting of, but not limited to, rizatriptan, eletriptan, naratriptan, zolmitriptan, frovatriptan, sumatriptan, almotriptan, and functional analogs thereof, wherein the functional analogs have essentially the same biological activity.

In one aspect, the present invention provides for a method of treating psoriasis, the method comprising administering to a subject in need of such treatment a tryptamine based drug that acts as a 5-hydroxytryptamine-1 inhibitor in a therapeutically effective amount sufficient to reduce the effects of psoriasis.

In yet another aspect, the present invention provides for a composition comprising a tryptamine based drug that acts as a 5-hydroxytryptamine-1 inhibitor in a therapeutically effective amount sufficient to reduce the effects of psoriasis and wherein the composition is formulated into a gel, paste, cream, lotion, emulsion, aerosol or ointment.

A still further aspect of the present invention provides for a method for treatment of psoriasis comprising:
(a) topically administering to an area of human skin affected by psoriasis a topical dosage form comprising a tryptamine based drug that acts as a 5-hydroxytryptamine-1 inhibitor in a concentration of between about 0.001% and about 1%; and
(b) continuing the administration until symptoms of psoriasis are abated.

Yet another aspect of the present invention provides for a composition comprising:
at least one tryptamine based drug that acts as a 5-hydroxytryptamine-1 inhibitor in a concentration of about 0.001% to about 1%; and at least three of the following components selected from the group consisting of:
a. at least one emollient in a concentration of in a concentration of about 5% to about 60%;
b. at least one thickener in a concentration of about 0.5% to about 20%;
c. at least one preservative in a concentration of about 0.01% to about 10%;
d. at least one moisturizer in a concentration of about 0.01% to about 10%;
e. at least one surfactant in a concentration of about 1% to about 20%;
f. at least one antimicrobial in a concentration of about 0.01% to about 2%; and water from about 2% to 80%.

Other aspects and advantages of the invention will be more fully apparent from the ensuing disclosure and appended claims

BRIEF DESCRIPTION OF THE FIGURE

FIG. 1 shows the effects of treatment Rt elbow: Carrier use for 4 days. No change in skin condition and scales. Lt elbow: Active ingredient, sumatriptan at 40 mg/100 ml cream use. Disappearance of scales and skin return to normal is noted. The normalization of skin is centripetal, i.e. first skin tissue to return to normal is peripheral.

DETAILED DESCRIPTION OF THE INVENTION

In the practice of the invention, at least one triptan is used to treat skin damage when topically applied in effective amounts. Surprisingly, the triptan concentration used on the skin is minimal as compared to systemic use but achieves a therapeutic effect in a short time, i.e. scale disappearance and skin normalization within days of use.

Heretofore, triptans were prescribed for the treatment of headaches through oral ingestion, subcutaneous injection, intranasal spray (5% irritation) or transdermal using iontophoresis (25% skin irritation). Notably, in the past transdermal treatment included a technique that required the use of electrical current and an iontophoretic transdermal patch (Pierce et al). Notably, the use of triptans for topical use has not been considered as an acceptable treatment for skin contact because of the etiology for irritation (see Safety Data Sheet of triptans, e.g. sumatriptan, naratriptan, rizatriptan). Exposure of skin to triptans is considered a contamination and recommended to be avoided and contaminated skin to be washed. A search of the literature did not reveal any reference to triptan activity on psoriasis or a psoriatic therapeutic effect, but on the contrary, to adverse effects induced on skin due to oral intake, i.e. paresthesias (Edmeads, Millson). Furthermore, psoriasis is an exclusion criteria in clinical research directed to sumatriptan use.

Thus, it is surprising that triptans, at low concentrations, would be so effective on treatment and/or controlling of psoriasis of the skin and its appendages, e.g. scalp and nails. The composition according to the present invention suitably comprises triptans at a concentration from about 0.0001-10% per weight, more preferably from about 0.001-1% per weight, and most preferably from about 0.01 to 0.1% per weight.

The present invention includes compositions for the treatment of psoriasis, comprising as active ingredient (as herein defined) chemical compounds which are HT-1 inhibitors and salts thereof. Combinations of such triptan may be included and in the presence of a salt or other carrier might be used, such as hydrochloride, hydrobromide, mesylate, acetate, trifluoroacetate, propionate, fumarate, tartrate, citrate, phosphate, succinate, bisulfate, etc.

The composition according to the present invention may also comprise additional pharmaceutically acceptable compounds and/or compositions. It is thus to be understood that all the additional compounds and/or compositions mentioned below have to be physiologically acceptable.

The active agents may be formulated into various pharmaceutically compositions, e.g. a solution, a lotion, a tonic, a shampoo, a gel, a mousse, a wax, a stick, a mask, a soap, a moisturizer, a cream, an ointment, or a paste.

The composition according to the present invention may be topically applied as such within a suitable carrier, solvent, dissolvent, emulgent, extract, solutions e.g. aqueous, alcoholic, oily, suspension; microemulsion, vesicles, etc. Where employed, the carrier is inert in the sense of not bringing about a deactivation or oxidation of the triptan, and in the sense of not bringing about any adverse effect on the skin areas to which it is applied.

In one aspect of the invention, at least one triptan is applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin. While the triptan carrier for dermatological compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration. Many preparations are known in the art, and include lotions containing oils and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids.

Various types of other ingredients may be present in compositions of the present invention. For example, sunscreens may be included such as those materials commonly employed to block ultraviolet light. Illustrative compounds are the derivatives of PABA, cinnamate and salicylate. The exact amount of sunscreen employed in the compositions can vary depending upon the degree of protection desired from the sun's UV radiation.

The compositions for use in the methods of the present invention may include components such suitable carriers such as starches, emollients, sugars, alcohols, microcrystalline cellulose, diluents, granulating agents, lubricants, surfactants including amphoteric, binders, disintegrating agents, and the like, with the topical preparations being preferred.

Emollients are often incorporated into the therapeutic compositions of the present invention. Levels of such emollients may range from about 0.5% to about 60%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate.

Suitable fatty alcohols and acids include those compounds having from 10 to 20 carbon atoms. Especially preferred are compounds such as cetyl, arachidyl, behenyl, cetearyl, myristyl, palmitic and stearyl alcohols and acids.

Among the polyols which may serve as emollients are linear and branched chain alkyl polyhydroxyl compounds. For example, propylene glycol, resorcinol, menthol, bisabolol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, paraffin oil, squalene and isoparaffins.

Another category of functional ingredients within the therapeutic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials. Gums may be employed such as xanthan, carrageenan, gelatin, karaya, pectin and locust beans gum. Under certain circumstances the thickening function may be accomplished by a material also serving as a silicone or emollient. For instance, silicone gums having a viscosity in excess of 10 mPas and esters such as glycerol stearate have dual functionality.

Still further, the therapeutic compositions of the present invention may include preservatives, moisturizers, surfactants, antimicrobials, etc. Preservatives may include tetrasodium ethylene-diamine tetraacetic acid (EDTA), methylparaben, benzophenone-4, methylchloroisothiazolinone, sodium benzoatemethylisothiazolinone, and the like, and mixtures thereof. Preservatives, when used, are typically present in an amount from about 0.01% to 10% weight, preferably about 0.05% to 4% weight, and more preferably, from about 0.1% to 2% weight.

Preferred moisturizers may include wheat protein (e.g., laurdimonium hydroxypropyl hydrolyzed wheat protein), hair keratin amino acids, sodium peroxylinecarbolic acid, panthenol, tocopherol (Vitamin E), dimethicone, arachidylglucoside and the like, and mixtures thereof. Moisturizers, when used, are typically present in an amount from about 0.01% to 10% weight, preferably about 0.05% to 1.5% weight, more preferably, from about 0.1% to 1% weight of the composition.

Preferred surfactants, including both the foaming and non-foaming type, include sodium laureth sulfate, sodium laureth-13 carboxylate, disodium laureth sulfosuccinate, disodium cocoamphodiacetate, glycol stearate, PEG-150 distearate and the like, and mixtures thereof. More preferably, at least one amphoteric surfactant is included in the composition, selected from the group consisting of lauroamphocarboxypropionate, lauroamphopropionate, lauroamphoglycinate, lauroamphocarboxyglycinate, lauroamphopropylsulfonate, lauroamphocarboxypropionic acid, myristoamphocarboxypropionate, myristoamphopropionate, myristoamphoglycinate, myristoamphocarboxyglycinate, myristoamphopropylsulfonate, myristoamphocarboxypropionic acid, cocoamphocarboxypropionate, cocoamphopropionate, cocoamphoglycinate, cocoamphocarboxyglycinate, cocoamphopropylsulfonate, cocoamphocarboxypropionic acid and mixtures thereof. The surfactant component may be present in an amount from about 0.1% to about 20% weight of the composition.

Any pharmaceutically acceptable antimicrobial agent available to those of ordinary skill in the art may be used in the present compositions including: echinacea, golden seal, benzalkonium chloride, triclosan, benzethonium chloride, iodine, grape seed extract, pomegranate extract, green tea extract or polyphenols, and the like, or combinations thereof. The antimicrobial agent is typically present in an amount from about 0.01% to 2% weight, preferably from about 0.1% to 1.2% weight, and more preferably from about 0.3% to 1% weight of the composition. The antimicrobial agent inhibits the formation, and may further reduce, the presence of microbes that cause redness, inflammation, and irritation of the skin.

The topical skin treatment composition of the invention can be formulated as a lotion having a viscosity of from 4,000 to 10,000 mPas, a fluid cream having a viscosity of from 10,000 to 20,000 mPas or a cream or a gel having a viscosity of from 20,000 to 100,000 mPas or above.

The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

Generally, in the practice of methods of the invention, the composition is topically applied to the affected skin areas in a predetermined or as-needed regimen either at intervals by application of a lotion or the like, it generally being the case that gradual improvement is noted with each successive application. For example, in use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Because of its ease of administration, a cream, lotion, gel or ointment represents the most advantageous topical dosage unit form, and such forms may be prepared as rinse-off or leave-on products, as well as two stage treatment products for use with other skin cleansing or managing compositions. Each of these forms is well understood by those of ordinary skill in the art, such that dosages may be easily prepared to incorporate the pharmaceutical composition of the invention.

Importantly, insofar as has been determined based upon clinical studies to date, no adverse side effects are encountered.

The composition according to the present invention may also be formulated as an internally ingested tablet, capsule, drops or suspension for use as a Psoriasis remedy. These compositions may comprise several types of carriers including, but not limited thereto, solutions, aerosols, emulsions, gels, solids, and liposomes.

The compositions according to the present invention in particular those used for the treatment of Psoriasis may thus further comprise, for example, one or more supplementary pharmaceutically active compound capable of functioning in different ways to enhance the activity of triptans, such as steroids, retinoids; calcipotriol; coal tar; emollients, sulfur and/or dithranol.

The composition according to the present invention may be applied also as part of a physical therapy, such as with ultraviolet, blue light spectrum, UVA, UVB or infrared radiation, of ultrasound.

The present invention has been described in terms of preferred embodiments, but the skilled artisan will appreciate that various alterations, substitutions, omissions, and changes may be made without departing from the scope of the present invention. The amounts of said compounds being used may be varied in accordance with the specific requirements.

The present invention will now be illustrated with reference to the following examples and FIGURE, annexed hereto without being limited by them.

Example 1

A 40 yrs old male subject with chronic psoriasis was administered a cream composed of 0.04% w/w sumatriptan, Dimethicon, Capric Caprylic triglyceride, Mineral oil, Cetyl alcohol & Glyceryl stearate & PEG-75 & Ceteth-20 & Steareth-20, Cetearyl alcohol, Shea butter, Glycerin, Triclosan, Propylene Glycol, Sodium Benzoate, Methylisothiazolinone in water. It was used for five days, once daily, on one elbow. The subject was examined and disappearance of scales was prominent on the treated side. Healthy skin with normalization was noted as well on the elbow. No change was observed on psoriasis lesions on the untreated side. The subject was instructed to use the cream once daily on the complementary elbow. Again, within about three days the scale disappeared and skin turned into normal within the next week.

Example 2

A 51 year old male subject with scales on both elbows was recruited. The subject used twice daily for 5 days two different creams:

a. Active ingredients: The left elbow was applied twice daily a cream composed of 0.04% w/w sumatriptan within an inactive base composed of Dimethicon, Capric Caprylic triglyceride, Mineral oil, Cetyl alcohol & Glyceryl stearate & PEG-75 & Ceteth-20 & Steareth-20, Cetearyl alcohol, Shea butter, Glycerin, Triclosan, Propylene Glycol, Sodium Benzoate, Methylisothiazolinone in water.

b. Inactive ingredient: The right elbow was applied an identical carrier cream, at the same dosing and without the sumatriptan.

The abovementioned design eliminates the mild possible therapeutic effect of an emollient on scales and healing. The mode of treatment eliminates as well the possibility of self healing or placebo effect.

As shown in FIG. 1, four days following the start of use the sumatriptan based cream has normalized the skin. The normalization of skin was centripetal, i.e. first skin tissue to return to normal is peripheral. On the contrary, use of a carrier solely did not affect the scales or the clinical condition of the elbow.

The skin normalization was completed within additional 4-5 days and the remission of the psoriasis on the elbow lasted for about one month. Afterwards, the scale gradually appeared on the treated elbow.

Example 3

Cream

|   | CTFA/INCI CHEMICAL NAME | % w/w |
|---|---|---|
| A | Dimethicon | About 3.0 |
|   | Capric Caprylic triglyceride | About 4.0 |
|   | Mineral oil | About 4.0 |
|   | Cetyl alcohol & Glyceryl stearate & PEG-75 & Ceteth-20 & Steareth-20 | About 6.0 |
|   | Cetearyl alcohol | About 2.0 |
|   | *Butyrusperum parkii* (Shea Butter) | About 4.0 |
|   | Triclosan | About 0.3 |
| B | Deionized Water | About 64.36 |
|   | Glycerin | About 3.0 |
|   | Propylene Glycol | About 2.0 |
| C | Deionized Water | About 5.0 |
|   | Sodium Benzoate | About 0.2 |
| D | Methylisothiazolinone | About 0.1 |
| E | Sumatriptan | About 0.04 |
|   | Deionized Water | About 2.0 |
|   | Total | 100.0 |

Procedure

Heat phase A and B to 75° C. to obtain solutions.

While stirring add phase B to A at 75° C., homogenize for 15 minutes.

Continue stirring and cooling to 35° C., Add phase C, stir and add phase D. keep stirring and cooling to RT.

A white cream is obtained.

Sumatriptan 40 mg is mixed with 2 ml of deionized water to obtain a suspension.

Add to 100 g cream with stirring at RT.

Example 4

W/o Skin Emulsion

| CTFA/INCI CHEMICAL NAME | % w/w |
|---|---|
| A. Oil phase | |
| Isopropyl stearate | 5.00 |
| Paraffin oil | 15.00 |
| Preservative | 0.20 |
| Peg-22/dodecyl glycol copolymer | 3.00 |
| Hydroxyoctyl hydroxystearate | 5.00 |
| Methoxy peg-22/dodecyl glycol copolymer | 3.00 |
| B. Water phase | |
| Sorbitol 70% | 5.00 |
| Sumatriptan | 0.01 |
| Deionized water | 63.79 |
| Total | 100.00 |

Manufacturing Procedure:

Heat Part A and Part B, separately, at 75-80 C.°.

Add Part A on Part B under high stirring.

Cool to RT under moderate stirring.

Sumatriptan 10 mg is mixed with 2 ml of deionized water to obtain a suspension.

Add to 100 g cream with stirring at room temperature (RT).

Example 5

Scalp Lotion

| CTFA/INCI CHEMICAL NAME | % w/w |
|---|---|
| Resorcinol | 0.50 |
| Menthol | 5.00 |
| Bisabolol | 0.20 |
| Dea-oleth-3 phosphate | 2.50 |
| Hydroxypropylcellulose | 2.50 |
| Amphoteric-1 | 5.00 |
| Ethanol 96% | 40.00 |
| Deionized water | 42.28 |
| Rizatriptan | 0.02 |
| Deionized water | 2.0 |
| Total | 100.00 |

Manufacturing Procedure:

Add Hydroxypropylcellulose in water under high stirring.

Add Amphoteric-1 and mix to dissolution.

Add the surfactant DEA-Oleth-3 Phosphate.

Dissolve in alcohol: Bisabolol, Menthol and Resorcinol and add to mix.

Cool to RT under moderate stirring.

Rizatriptan 20 mg is mixed with 2 ml of deionized water to obtain a suspension.

Add to 100 g cream with stirring at RT.

Example 6

Hydrophilic Ointment

| Ctfa/Inci Chemical Name | % w/w |
|---|---|
| A. Oil Phase | |
| Petrolatum | 10.00 |
| Mineral Oil | 10.00 |
| Cetostearyl Alcohol | 4.00 |
| Isostearyl Isostearate | 6.00 |
| B. Aqueous Phase | |
| Sodium Lauryl Sulphate | 1.50 |
| Purified Water (Aqua) | 36.995 |
| Methyl Gluceth-20 | 10.00 |
| C. Active Ingredients | |
| Propylene Glycol | 15.00 |
| Sulfur Colloidal | 4.00 |
| Preservative | 0.50 |
| Zolmitriptan | 0.005 |
| Deionized Water | 2.0 |
| Total | 100.00 |

Manufacturing Procedure:

Heat Part A and Part B, separately, at 75-80 C.°.

Add Part A on Part B under high stirring.

Cool to RT under moderate stirring.

At 45 C.° add the mix of Part C.

Cool to RT under moderate stirring.

Zolmitriptan 5 mg is mixed with 2 ml of deionized water to obtain a suspension.

Add to 100 g cream with stirring at RT.

Example 7

Cream

| CTFA/INCI CHEMICAL NAME | % w/w |
|---|---|
| A. Oil phase | |
| Arachidyl and behenyl alcohol/arachidylglucoside | 2.00 |
| Cetearyl alcohol and cetearyl glucoside | 2.00 |
| Propylene glycol dicaprylate/caprate | 8.00 |
| Octyl isostearate | 6.00 |
| Propyl paraben | 0.20 |
| B. aqueous phase | |
| Calcium lactate | 0.25 |
| Deionized water | 72.81 |
| Polyacrylamide and c13-14 isoparaffin and laureth-7 | 0.70 |
| C. Additional components | |
| Preservative | 0.50 |
| Propylene glycol | 5.50 |
| Deionized water | 2.0 |
| Zolmitriptan | 0.04 |
| Total | 100.00 |

Manufacturing Procedure:

Heat Part A and B, separately to 60-65 C.°.

Add the Part A to Part B and homogenize vigorously.

Stir under cooling to RT.
Mix together the component of Part C.
Add Part C at 40 C.°.
Cool to RT under moderate stirring.
Zolmitriptan 40 mg is mixed with 2 ml of deionized water to obtain a suspension.
Add to 100 gr cream with stirring at RT.

REFERENCES

The contents of all references cited herein are hereby incorporated by reference herein for all purposes.

Edmeads J G, Millson D S. Tolerability profile of zolmitriptan (Zomig; 311C90), a novel dual central and peripherally acting 5HT1B/1D agonist Cephalalgia 1997 Suppl 18:41-52.

Gudjonsson J E, Johnston A, Sigmundsdottir H, Valdimarsson H. Immunopathogenic mechanisms in psoriasis. Clin Exp Immunol. 2004 135 (1):1-8.

Frank O. Nestle, M. D., Daniel H. Kaplan, M. D., Ph.D., and Jonathan Barker, M. D. Psoriasis New Eng J Med Volume 2009 361 (5):496-509.

McFadden J, Valdimarsson H, Fry L. Cross-reactivity between streptococcal M surface antigen and human skin. Br J Dermatol. 1991 125 (5):443-7.

Mark Pierce, MD, PhD; Thomas Marbury, MD; Carol O'Neill, BA; Steven Siegel, MD, PhD; Wei Du, PhD; Terri Sebree, BA Zelrix™: A Novel Transdermal Formulation of Sumatriptan. Headache, 2009, 49 (6):817-825.

SDS No 128214 Sumatriptan, Safety Data Sheet, GlaxoSmithKlein 2004.

SDS No 110533 Naratriptan, Safety Data Sheet, GlaxoSmithKlein 2008.

SDS SRP 013035r, Rizatriptan Benzoate, SeqChem, London, UK.

Schön M P and Boehncke W H. Psoriasis. New Eng J Med. 2005, 352 (18):1899-1912 2005.

The invention claimed is:

1. A method of treating psoriasis, the method comprising: topically administering to a subject in need of such treatment a composition that consists of a single active agent to treat the psoriasis, wherein the single active agent is sumatriptan and is topically administered in an amount from about 0.01% to about 1% per weight.

2. The method of claim 1, wherein the sumatriptan is combined with a pharmaceutical carrier to form a composition.

3. The method of claim 1, wherein the sumatriptan is combined with at least three of the following components selected from the group consisting of:
   at least one emollient in a concentration of in a concentration of about 5% to about 60%;
   at least one thickener in a concentration of about 0.5% to about 20%;
   at least one preservative in a concentration of about 0.01% to about 10%;
   at least one moisturizer in a concentration of about 0.01% to about 10%;
   at least one surfactant in a concentration of about 1% to about 20%;
   at least one antimicrobial in a concentration of about 0.01% to about 2%;
   and water from about 2% to 80%, to form a composition.

* * * * *

UNITED STATES PATENT AND TRADEMARK OFFICE
CERTIFICATE OF CORRECTION

| | |
|---|---|
| PATENT NO. | : 8,680,134 B2 |
| APPLICATION NO. | : 13/503418 |
| DATED | : March 25, 2014 |
| INVENTOR(S) | : Avi Dascalu |

It is certified that error appears in the above-identified patent and that said Letters Patent is hereby corrected as shown below:

In the specification

Column 1, lines 7-10 - should be -- "This application is filed under the provisions of 35 U.S.C. §371 and claims the priority of International Patent Application No. PCT/IB2010/002881 filed on October 22, 2010 which in turn claims priority to U.S. Provisional Application No. 61/254,258 filed on October 23, 2009, the contents of which are incorporated by reference herein for all purposes."

Signed and Sealed this
Twenty-seventh Day of October, 2015

Michelle K. Lee
*Director of the United States Patent and Trademark Office*